United States Patent [19]

Hayes

[11] Patent Number: 4,999,195
[45] Date of Patent: Mar. 12, 1991

[54] PERSONAL CARE PRODUCTS CONTAINING BIOEMULSIFIERS

[75] Inventor: Michael E. Hayes, Fernandina Beach, Fla.

[73] Assignee: Emulsan Biotechnologies Inc., New York, N.Y.

[21] Appl. No.: 375,436

[22] Filed: Jul. 5, 1989

Related U.S. Application Data

[60] Division of Ser. No. 852,272, Apr. 15, 1986, Pat. No. 4,870,010, which is a continuation-in-part of Ser. No. 662,931, Oct. 16, 1984, abandoned.

[51] Int. Cl.$^5$ .................... A61K 7/06; A61K 7/48; A61K 7/50; A61K 31/71
[52] U.S. Cl. ............................. 424/114; 424/70; 514/847; 514/852; 514/859; 514/860; 514/861; 514/863; 514/864; 514/873; 514/880; 514/881; 514/886; 514/887
[58] Field of Search ............ 424/70, 114; 514/859, 514/861, 863

[56] References Cited

U.S. PATENT DOCUMENTS

| | | | |
|---|---|---|---|
| 3,941,692 | 3/1976 | Gutnick et al. | 210/611 |
| 3,960,832 | 6/1976 | Kang et al. | 536/123 |
| 3,998,761 | 12/1976 | Gary et al. | 424/70 |
| 4,116,848 | 8/1978 | Schoenholz et al. | 252/90 |
| 4,195,177 | 4/1980 | Inoue et al. | 536/116 |
| 4,215,213 | 7/1980 | Inoue et al. | 536/115 |
| 4,230,801 | 10/1980 | Gutnick et al. | 435/101 |
| 4,234,689 | 10/1980 | Gutnick et al. | 435/101 |
| 4,260,528 | 4/1981 | Fox et al. | 252/525 |
| 4,297,340 | 10/1981 | Abe et al. | 424/70 |
| 4,305,929 | 12/1981 | Kawano et al. | 424/63 |
| 4,305,931 | 12/1981 | Kawano et al. | 424/69 |
| 4,305,961 | 12/1981 | Tsutsumi et al. | 514/777 |
| 4,309,447 | 11/1982 | Tsutsumi et al. | 514/777 |
| 4,311,829 | 1/1982 | Gutnick et al. | 536/53 |
| 4,311,830 | 1/1982 | Gutnick et al. | 536/53 |
| 4,311,831 | 1/1982 | Gutnick et al. | 536/53 |
| 4,318,901 | 3/1982 | Ishida et al. | 424/70 |
| 4,329,448 | 5/1982 | Cox et al. | 252/8.555 |
| 4,355,109 | 10/1982 | Zajic et al. | 435/170 |
| 4,357,423 | 11/1982 | Cox et al. | 435/101 |
| 4,364,837 | 12/1982 | Pader | 252/173 |
| 4,374,823 | 2/1983 | Harvey et al. | 424/49 |
| 4,380,504 | 4/1983 | Gutnick et al. | 252/356 |
| 4,393,089 | 7/1983 | Cox et al. | 426/573 |
| 4,395,353 | 7/1983 | Gutnick | 252/356 |
| 4,395,354 | 7/1983 | Gutnick et al. | 252/356 |
| 4,401,648 | 8/1983 | Piechota, Jr. | 424/49 |
| 4,483,782 | 11/1984 | Cox et al. | 252/174.17 |
| 4,803,195 | 2/1989 | Holzner | 512/4 |

OTHER PUBLICATIONS

Taylor, W. and Juni, E., J. Bacteriol. 81: 688–693 (1961).

Gutnick, et al., in: Advances in Biotechnology Col. III, Proceedings of the Sixth International Fermentation Symposium, (London–Canada), 1980, pp. 455–459.

Rosenberg, E. et al., Infect. Immun. 39: 1024–1028 (1983).

*Primary Examiner*—Dale R. Ore
*Attorney, Agent, or Firm*—Pennie & Edmonds

[57] ABSTRACT

Personal care products comprising bioemulsifiers, for example, those produced by *Acinetobacter calcoaceticus*, are provided. Use of such personal care products result in beneficial effects to skin and hair.

12 Claims, No Drawings

PERSONAL CARE PRODUCTS CONTAINING BIOEMULSIFIERS

This is a division of application Ser. No. 06/852,272 filed Apr. 15, 1986, now U.S. Pat. No. 4,870,010, which in turn is a continuation-in-part of application Ser. No. 662,931, filed Oct. 16, 1984, entitled "Soaps and Shampoos Containing Bioemulsifiers," which is incorporated herein by reference, now abandoned.

TABLE OF CONTENTS

1. Field of the Invention
Background of the Invention
  2 1 Biological Materials in Consumer Products
  2.2. Microbial Surface Active Compounds
3. Summary of the Invention
4. Nomenclature
5. Detailed Description of the Invention
  5.1. Microbial Bioemulsifiers
  5.2. Properties of Emulsans
  5.3. Personal Care Product Compositions
  5.4. Beneficial Effects of Bioemulsifier-Containing Personal Care Products
6. Examples
  6.1 Preparation of Technical Grade Emulsan
  6.2 Emulsan Formulation for Use in Soaps and Shampoos
  6.3. Emulsan in Toilet Soap
    6.3.1. Bar Soap Composition
    6.3.2. Bar Soap Testing
  6.4. Effect of Emulsan-Containing Soap Bars on Skin Conditions
    6.4.1. Effect of Emulsan-Containing Soap Bars on Acne
    6.4.2. Effect of Emulsan-Containing Soap Bars on Razor Burn
  6.5. Emulsan in Shampoo
    6 5.1. Shampoo Base Compositions
    6.5.2. Shampoo Testing
  6.6. Effect of Emulsan-Containing Shampoo on Scalp Conditions
    6.6.1. Effect of Emulsan-Containing Shampoo on Dandruff
    6.6.2. Effect of Emulsan-Containing Shampoo on Eczema/Psoriasis of the Scalp
  6.7. Conditioning Effects of Emulsan-Containing Shampoo
    6.7.1. Decreased Static Build-up
    6.7.2. Improved Shine
  6.8. Effect of Emulsan-Containing Shampoo on Mildew
  6.9. Emulsan in Cleansing Creams and Lotions
    6.9.1. Cleansing Cream and Lotion Compositions
    6.9.2. Effect of Emulsan-Containing Cleansing Creams and Lotions on Acne and Oily Skin
    6.9.3. Effect of Emulsan-Containing Cleansing Creams and Lotions on Normal Skin
  6.10. Emulsan in Moisturizing Creams and Lotions
    6.10.1. Moisturizer Compositions
    6.10.2. Effect of Emulsan-Containing Moisturizers on Skin
  6.11. Emulsan in Mud Mask

1. FIELD OF THE INVENTION

This invention relates to personal care products suitable for cleansing and/or imparting other beneficial effects to human skin and hair. More particularly, the invention relates to personal care products containing bioemulsifiers as effective ingredients.

2. BACKGROUND OF THE INVENTION

2.1. BIOLOGICAL MATERIALS IN CONSUMER PRODUCTS

Biological materials have been incorporated into numerous consumer products for numerous purposes. For instance, biopolymeric materials, such as polysaccharides, proteins and nucleic acids have been added to products as diverse as paints, foods, skin creams and cleaning agents in which they serve such diverse functions as thickeners, suspending agents, moisturizers and conditioners. Certain specific biological materials have been incorporated into skin and hair care products for human use.

For example, chemically-modified glycolipids, specifically hydroxypropyl-etherified sophorolipid esters, have been used in cosmetic compositions for skin and hair care. The sophorolipids used as starting materials are the products of a yeast, *Torulopsis bombicola*. The chemically-modified sophorolipids improve the setting capacity of hair setting lotions and hair sprays and influence the lathering characteristics of shampoos. Hair washed with sophorolipid-containing shampoos retains a moist finishing touch. These various effects are described in U.S. Pat. Nos. 4,297,340 and 4,318,901. The same chemically-modified sophorolipids can serve as moisturizing, conditioning and protective agents in skin creams and lotions [U.S. Pat. Nos. 4,297,340; 4,305,961 and 4,309,447], in stick-shaped cosmetics, such as lipsticks and eyeshadows [U.S. Pat. No. 4,305,929], and in pressed powder cosmetics [U.S. Pat. No. 4,305,931].

A microbial biopolymer produced by *Bacillus polymyxa* has been proposed as a useful ingredient in certain cosmetics and shampoos [U.S. Pat. Nos. 4,329,448; 4,357,423 and 4,393,089]. This biopolymer is a heteropolysaccharide comprising glucose, galactose, mannose, glucuronic acid and fucose. In the foregoing patents it is suggested that such biopolymer can be used in anti-dandruff shampoos as a suspending agent for anti-dandruff ingredients, in other shampoos and shower washes as a gelling agent, and in hand creams as an emulsion stabilizer.

A beer concentrate comprising a mixture of proteins and polysaccharides has been used as an ingredient in shampoos. The beer concentrate acts as a conditioner and also imparts body to hair shampooed with the formulations disclosed in U.S. Pat. No. 3,998,761. The use of mono-, di- and polysaccharides in shampoos has been described in U.S. Pat. No. 4,364,837. It is reported that the presence of saccharides in shampoos stabilizes the shampoos and also enhances foam quality. The saccharides thicken the shampoo and act as suspending agents for grooming ingredients in the shampoo. Preferred saccharides were reported to be corn and potato syrups containing glucose and di- and polysaccharides of glucose.

2.2. MICROBIAL SURFACE ACTIVE COMPOUNDS

Many microbes can utilize hydrocarbon as their sole source of carbon for growth and energy production. The hydrocarbon substrates may be linear, branched, cyclic or aromatic. In order to rapidly assimilate such water-insoluble substrates, the microbes require a large contact area between themselves and the oil. This is achieved by emulsifying the oil in the surrounding aqueous medium. Hydrocarbon degrading microbes frequently synthesize and excrete surface active agents which promote such emulsification. Some of the microbial surface active and interfacially active agents that have been reported in the literature are listed in Table I.

TABLE I

| MICROBIAL SURFACE ACTIVE COMPOUNDS | |
|---|---|
| STRUCTURAL TYPE | PRODUCING MICROORGANISM(S) |
| Carbohydrates-Lipids | |
| Trehalose-Lipids | Nocardia, Mycobacterium, Corynebacterium, Arthrobacter |
| Rhamnose-Lipids | Pseudomonas aeruginosa |
| Sophorose-Lipids | Torulopsis spp. |
| Polysaccharide-Lipids | Candida tropicalis, Acinetobacter calcoaceticus |
| Amino Acid-Lipids | |
| Lipopeptides | Bacillus, Streptomyces, Corynebacterium, Mycobacterium |
| Ornithine-Lipids | Pseudomonas, Thiobacillus, Agrobacterium, Gluconobacter |
| Phospholipids | Thiobacillus, Corynebacterium, Candida, Micrococcus |
| Fatty Acids/ Neutral Lipids | Pseudomonas, Mycococcus, Penicillium, Aspergillus, Acinetobacter, Micrococcus, Candida |

Gutnick et al. discovered that *Acinetobacter calcoaceticus* ATCC 31012 (deposited with the American Type Culture Collection, Rockville, MD and also known in the literature as RAG-1) produces interfacially active extracellular protein-associated lipopolysaccharide biopolymers called emulsans. The emulsans are polyanionic materials. *Acinetobacter calcoaceticus* ATCC 31012 produces @-emulsans when grown on ethanol or fatty acid salts [U.S. Pat. Nos. 4,230,801; 4,234,689 and 4,395,354] and ↑-emulsans when grown on crude oil or hexadecane [U.S. Pat. No. 3,941,692]. The @-emulsans and ↑-emulsans, which differ in their respective lipid content, can be derivatized to an O-deacylated form called psi-emulsans [U.S. Pat. No. 4,380,504]. The @-emulsans, ↑-emulsans and psi-emulsans can be deproteinized to yield apo-@-emulsans, apo-↑-emulsans and apo-psi-emulsans, respectively [U.S. Pat. Nos. 4,311,830; 4,311,829 and 4,311,831, respectively]. The emulsans exhibit exceptional bioemulsifier activity especially with hydrocarbon substrates which contain both aliphatic and cyclic or aromatic components.

In addition to acting as bioemulsifiers, the emulsans are capable of interfering with the adherence of microorganisms to certain surfaces. Recently, Rosenberg et al. [Infect. Immun. 39(3):1024–28 (1983)] have shown that emulsan can markedly inhibit the adherence of *Acinetobacter calcoaceticus* ATCC 31012 and Acinetobacter calcoaceticus BD 413 [Taylor and Juni, J. Bacteriol. 81:688–93 (1961)] and *Streptococcus pyogenes* M-5, either to human buccal epithelial cells or to octane. The degree of interference with adherence was the same, whether the emulsan was used to prevent binding or added later, to desorb already bound bacteria.

Gutnick et al. have also reported that a phage-resistant mutant of *Acinetobacter calcoaceticus* ATCC 31012 produces a highly viscous, inactive (i.e., nonbioemulsifying) derivative of the emulsans which is nevertheless cross-reactive with antibodies raised against emulsan ["Emulsan Production in Acinetobacter RAG-1," in: Advances in Biotechnology, Vol. III, Proceedings of the Sixth International Fermentation Symposium, London, Canada (1980), M. Moo-Young (ed.), pp. 455–459].

3. SUMMARY OF THE INVENTION

It is an object of the present invention to provide personal care products with desirable cleansing, moisturizing, feel improvement and/or antiseptic properties and which impart certain beneficial effects to human skin and hair.

It is a further object of the invention to provide soaps with creamy feeling foams, as well as cleansing creams, cleansing lotions, and masks which leave the skin feeling smooth and creamy after use. It is another object of the invention to provide soaps, cleansing creams, cleansing lotions, and masks which soothe, control, ameliorate and/or eliminate certain common dermatological problems such as acne, oily skin, eczema, psoriasis and razor burn.

Still another object of the invention is to provide shampoos with improved degreasing abilities and with enhanced cleansing power for residues left on hair by fixative agents. It is a further object of the invention to provide shampoos which leave hair in a conditioned state after washing and which impart shine to the hair. Another object of the invention is to provide shampoos capable of improving or eliminating such common scalp and hair problems as dandruff, psoriasis/eczema of the scalp and static build-up following blow-drying or combing.

It is a further object of the invention to provide creams and lotions with improved feel characteristics for use as moisturizers on human skin and which may also be used as topical preparations for acne control.

The above objects can be achieved by the addition to standard formulations of the aforementioned soaps, cleansing creams, cleansing lotions, masks, acne control preparations, shampoos and moisturizers an effective amount of microbial bioemulsifiers, preferably lipopolysaccharides produced by certain members of the *Acinetobacter* genus. In preferred embodiments, emulsans produced by *Acinetobacter calcoaceticus* ATCC 31012 are included in personal care products at a concentration ranging from about 0.04% to about 0.2% by weight.

The invention also contemplates the inclusion of emulsans and other microbial bioemulsifiers in consumer products such as hand cleaners, ointments, powders, including baby powder, talcum powder, cosmetic powder, and athlete's foot powder, baby lotions and other diaper rash medications, wound care products, deodorants, shaving creams, after shave lotions, dentifrices, toothpastes, gels, mouthwashes and other similar personal care products.

4. NOMENCLATURE

The term "bioemulsifier" is defined as any biologically derived substance which, by virtue of any combination of characteristics including, but not limited to, high molecular weight, polymeric nature, highly specific three-dimensional structure, hydrophobic and hydrophilic moieties and sparing solubility in hydrocarbons, binds tightly to the hydrocarbon/water interface and essentially covers the surface of individual hydrocarbon droplets in hydrocarbon-in-water emulsions, effectively maintaining discrete droplets and preventing coalescence, and thereby imparting substantial stability to hydrocarbon-in-water emulsions. An example of a bioemulsifier is @-emulsan.

The term "biosurfactant" is defined as any biologically derived substance which reduces the interfacial tension between water and a hydrocarbon and, as a result, reduces the energy requirement (mixing energy) for creation of additional interfacial area. An example of a biosurfactant is a glycolipid.

The term "emulsans" which reflects the polysaccharide structure of these compounds and the exceptional bioemulsifier activity of these materials, generically identifies those extracellular microbial protein-associated polyanionic lipoheteropolysaccharides produced by *Acinetobacter calcoaceticus* ATCC 31012 and its derivatives or mutants, which may be subdivided into the @-emulsans and the †-emulsans. The @-emulsans are the products of *Acinetobacter calcoaceticus* ATCC 31012 when grown on either ethanol or fatty acid salts as carbon source and the †-emulsans are the products when the organism is grown on crude oil or hexadecane, as determined under shake flask conditions.

The term "viscoemulsan" is defined as any lipoheteropolysaccharide, derived from a bacterium of the genus *Acinetobacter* and immunologically cross-reactive with antibodies against an Acinetobacter-derived bioemulsifier, which does not exhibit significant bioemulsifier activity, yet, by virtue of any combination of characteristics, including but not limited to, high molecular weight, polymeric nature and highly specific three-dimensional structure, exhibits the ability to increase the viscosity or otherwise alter the rheology of solutions or dispersions in which it is dissolved or suspended, respectively. An example of a viscoemulsan is the emulsan-cross-reactive material produced by *Acinetobacter calcoaceticus* ATCC 31926.

The term "soaps" is defined to include, but is not limited to, its common meaning of an alkali salt of a fatty acid, as well as detergents and so-called waterless cleaners.

The term "shampoo" is defined to include, but is not limited to, pourable water-based shampoos, gel shampoos, cream shampoos and so-called dry shampoos.

The term "acne" is defined to include, but is not limited to, clinical forms of the disease as well as lesser forms such as pimples, blemishes and other similar lesions.

5. DETAILED DESCRIPTION OF THE INVENTION 5.1. MICROBIAL BIOEMULSIFIERS

The water-soluble microbial interfacially active agents for use in the personal care products of this invention are any microbial substances which function as bioemulsifiers, i.e., substances which, by virtue of such characteristics as large molecular weight, polymeric nature, highly specific three-dimensional structure, hydrophobic and hydrophilic nature, and sparing solubility in oil, effectively cover the oil/water interface maintaining discrete, individual oil droplets in oil-in-water emulsions thereby substantially stabilizing emulsions from coalescence. Among the preferred bioemulsifiers are lipoheteropolysaccharide biopolymers produced by bacteria of the genus *Acinetobacter* and the genus *Arthrobacter*, and in particular, those produced by strains of *Acinetobacter calcoaceticus*. Such *Acinetobacter* lipoheteropolysaccharide biopolymers include, but are not limited to, polyanionic lipoheteropolysaccharide biopolymers, @-emulsan, †-emulsans, psi-emulsans, apo-@-emulsans, apo-†emulsans and apo-psi-emulsans produced by *Acinetobacter calcoaceticus* ATCC 31012 and described in U.S. Pat. Nos. 4,395,353; 4,395,354; 3,941,692; 4,380,504; 4,311,830; 4,311,829; and 4,311,831, respectively (hereby incorporated by reference). Such *Acinetobacter* biopolymers also include the biopolymers produced by *Acinetobacter calcoaceticus* BD4 [Taylor and Juni J Bacteriol. 81:688–693 (1961), hereby incorporated by reference], and *Acinetobacter calcoaceticus* NRRL-15616, as well as those produced by *Acinetobacter calcoaceticus*, strains NS-1 (NRRL B-15847), NS-4 (NRRL B-15848), NS-5 (NRRL B-15849), NS-6 (NRRL B-15860) and NS-7 (NRRL B-15850). The foregoing "NS" strains have been deposited at the Northern Regional Research Center, Peoria, IL and have been assigned the foregoing NRRL accession numbers. The "NS" strains of *Acinetobacter calcoaceticus* are described by Sar and Rosenberg, Current Microbiol. 9(6):309–14 (1983), hereby incorporated by reference. Products of the "NS" strains tested to date, like the emulsans, exhibit the ability to desorb microorganisms from surfaces.

Particularly preferred *Acinetobacter* lipoheteropolysaccharide biopolymers are the @-emulsans, the production of which is further described in U.S. Pat. Nos. 4,230,801 and 4,234,689 (hereby incorporated by reference). The @-emulsans are characterized by a Specific Emulsification Activity of about 200 units per milligram or higher, where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Magnesium buffer. Other particularly preferred *Acinetobacter* lipoheteropolysaccharide biopolymers include the apo-@-emulsans, psi-emulsans and apo-psi-emulsans.

In addition to *Acinetobacter* products which function as bioemulsifiers, other *Acinetobacter*-derived materials are suitable for use in the personal care products of this invention. Certain strains of *Acinetobacter calcoaceticus* are capable of producing materials that exhibit little, if any, bioemulsifier activity, yet are cross-reactive with antibodies specific for *Acinetobacter calcoaceticus* emulsifiers. Such materials can be used as viscosity agents and are called viscoemulsans. *Acinetobacter calcoaceticus* ATCC 31926 produces a viscoemulsan that is cross-reactive with antibodies against emulsans produced by *Acinetobacter calcoaceticus* ATCC 31012. In solution, this viscoemulsan causes an increase in viscosity. In addition, this viscoemulsan is capable of desorbing microorganisms from surfaces. Thus, it may be formulated into such products as liquid soaps and shampoos, cleansing creams and lotions, and moisturizing creams and lotions.

5.2. PROPERTIES OF EMULSANS

The ability of the emulsans, particularly @-emulsan, to stabilize emulsions makes them ideal ingredients in cleansing agents for the removal of greasy dirt and oils, including sebum, from human skin and hair. The principal factors controlling emulsion stability are electrostatic (charge) effects and steric effects. The properties of emulsans lend themselves to optimal exploitation of these mechanisms. Their large molecular weight and highly specific three-dimensional structure result in an efficient coverage of the oil/water interface. Hence, the oil droplets in oil-in-water emulsions are essentially "coated" with emulsan molecules. This effectively prevents oil-to-oil contact when collisions occur between adjacent droplets. Simultaneously, the polyanionic nature of emulsans cause the surfaces of emulsion droplets to be negatively charged which creates repulsive forces and significantly decreases the collision frequency between hydrocarbon droplets. In addition, the absence of multimolecular emulsan micelles in the water phase and the lack of emulsan solubility in the hydrocarbon phase provides an efficient migration and attachment of the emulsan molecules to the oil/water interface. The overall result is that coalescence of the oil droplets is very significantly retarded. This in turn means that any grease or oils to be removed from the skin or hair will remain in an emulsified state and can be easily rinsed off with water.

5.3. PERSONAL CARE PRODUCT COMPOSITIONS

Soap compositions to which bioemulsifiers can be added advantageously are standard toilet soap bases, normal or superfatted, comprising alkali metal salts of fatty acids from such sources as, for example, tallow, lard, coconut oil, palm oil and/or other edible oils. Other ingredients may also be added, for example, perfumes or medications. The bioemulsifier may be added to the soap bases in relatively low concentrations and still achieve desirable results. For technical grade @-emulsan, the product of *Acinetobacter calcoaceticus* ATCC 31012, a concentration range of about 0.02% to about 0.5% by weight is preferred. Higher quantities of technical grade @-emulsan may leave skin feeling dry after washing.

Shampoo compositions to which bioemulsifiers can be added advantageously are standard shampoo bases which comprise synthetic detergents. A store-bought baby shampoo has served as a suitable shampoo composition. Exemplary of ingredients that may be found in standard shampoo bases in a variety of combinations are fatty acid polyglycol esters (e.g., glycol distearate), fatty acid diethanolamides (e.g., cocamide DEA), neutralized salts of alkyl ether sulfates (e.g., sodium lauryl ether sulfate), cocoamphocarboxyglycinate, sugars, (e.g., fatty acid sarcosides such as sodium lauroyl sarcosinate), salts (e.g., sodium chloride), buffering agents and preservatives (e.g., citric acid), biocides (e.g., methylchloro- and methylisothiazolinone), fatty acid/amine condensation products (e.g., polyglycolpolyamine condensation products), salts of polypeptides (e.g., salts of hydrolyzed animal protein) and water. Other ingredients such as perfumes and grooming agents can also be present. The bioemulsifier may be added to the shampoo bases in small amounts. For technical grade @-emulsan, a concentration range of about 0.02% to about 0.5% by weight can be used. A preferred concentration range is between about 0.05% to about 0.20% by weight. Depending on the grade of bioemulsifier used, it may be desirable to add other ingredients to the shampoo. For example, technical grade @-emulsan, though dispersible, is not completely soluble in all shampoo raw materials. Therefore, it is desirable to use a pearlescing agent to make an opaque, pearlescent shampoo. It should be appreciated that grades of bioemulsifiers can be produced that are freely soluble in shampoo raw materials and can be used in translucent shampoos.

Cleansing cream and cleansing lotion compositions to which bioemulsifiers can be added advantageously are standard cosmetic creams and lotions known in the art [See, e.g., Kirk-Othmer Encyclopedia of Chemical Technology, Vol. 7, pp. 146–150 (3rd Edition, John Wiley & Sons, Inc., 1979)]. Such creams and lotions are emulsions of water-based and oil-based phases which are preferably water-rinsable or water-removable oil-in-water emulsions. Typical ingredients are oils, such as mineral oil, waxes, such as beeswax, fatty acids, alcohols, emulsifiers, perfumes, medications and preservatives. Ingredients used in lotions, particularly the oils and waxes, are identical to those used in creams but are present in different concentration.

Creams and lotions to which bioemulsifiers can be added to prepare either moisturizers with improved feel or preparations for acne control are also standard cosmetic creams and lotions known in the art. These are emulsions which may be either oil-in-water or water-in-oil emulsions, preferably oil-in-water. Moisturizing creams and lotions typically contain oils, waxes, fatty acids, alcohols, emulsifiers, perfumes and preservatives as ingredients and may also include additional ingredients such as aloe extracts, mucopolysaccharides, collagen and other recognized moisturizing agents.

When using technical grade @-emulsan, the product of *Acinetobacter calcoaceticus* ATCC 31012 in cosmetic creams and lotions, a concentration range of about 0.1% to about 0.2% by weight is preferred.

5.4. BENEFICIAL EFFECTS OF BIOEMULSIFIER-CONTAINING PERSONAL CARE PRODUCTS

The personal care products of the present invention can be used to impart desirable characteristics and beneficial effects to human skin and hair. Washing with soaps, cleansing creams or cleansing lotions containing bioemulsifiers, particularly @-emulsan, can make skin smooth and creamy to the touch. This is also true of moisturizing creams and lotions containing bioemulsifiers, particularly @-emulsan. Not only are such creams and lotions pleasant to the touch but they also leave the skin feeling smooth and creamy after application. Shampooing with shampoos containing bioemulsifiers can make hair conditioned, shiny and free of static build-up. Because of its superior cleansing and degreasing properties, bioemulsifier-containing shampoo can increase the time interval between washings. Hair fixatives such as sprays, laquers, creams, etc. can be removed easily with bioemulsifier-containing shampoos.

In addition to imparting aesthetically pleasing characteristics to skin and hair, the bioemulsifier-containing personal care products of the present invention, when used regularly, can bring about certain hygienically and medically beneficial effects. Soaps, cleansing creams, cleansing lotions and shampoos containing emulsans have demonstrably beneficial effects on such common skin and scalp conditions as acne, oily skin, dermatitis, dandruff, psoriasis, eczema, and razor burn and are therefore potentially useful as medicaments for the treatment and/or control of these and other dermatological conditions. The mechanism by which these beneficial effects are brought about is as yet unknown.

For a condition like acne, which is often associated with overproduction of sebum by sebaceous glands and the proliferation of microorganisms that feed on sebum, e.g., *Corynebacterium acnes* (which in turn lead to the blocked ducts, papules, pustules and general inflammation that are characteristic of the condition), it may be speculated that the emulsans effectuate improved removal of sebum from the skin, thereby preventing the bacterial growth that is symptomatic, if not causative, of the disease.

Alternatively, since it has been demonstrated in some instances that emulsans have the ability to desorb bacteria from epithelia, it may also be speculated that the soaps, cleansing creams, cleansing lotions, masks, shampoos and oral care products have their beneficial effects as a result of their desorbing disease-causing or disease-related microorganisms from the skin. The desorptive effect has led to the contemplation of the use of emulsans in wound treatment compositions and other products (e.g., wound dressings, deodorants and medicated, e.g., anti-fungal, powders) to prevent or inhibit microbial organisms from infecting wounds, causing body odor, or causing skin disorders like athlete's foot.

Other mechanisms besides degreasing and desorbing of bacteria may explain the beneficial effects of bioemulsifier-containing personal care products. The proposal of these two mechanisms is by no means intended as a limitation on the properties a bioemulsifier must have to be advantageously included in a personal care product.

The personal care products of this invention have been sampled by numerous test subjects in the form of soaps, cleansing creams and lotions, moisturizing creams and lotions, topical acne control preparations, masks and shampoos. Of all those receiving samples of personal care products, approximately 90-95% of them have reported favorable responses after regular use.

6. EXAMPLES

6.1. PREPARATION OF TECHNICAL GRADE EMULSAN

The @-emulsans produced by *Acinetobacter calcoaceticus* ATCC 31012 during fermentation on ethanol are known bioemulsifiers as described in U.S. Pat. No. 4,395,354, incorporated by reference, supra. The @-emulsans used in the personal care product compositions described infra were technical grade materials, prepared in either of two ways. Both methods of preparation involved enzyme treatment and drying but differed in the order in which these steps were performed.

By one method, centrifuged (approximately 90% cell-free) fermentation broth containing @-emulsans resulting from a fermentation of *Acinetobacter calcoaceticus* ATCC 31012 in ethanol medium was drum-dried and the resulting material was treated in the following manner prior to use. A 10% by weight suspension of the material, so-called technical grade @-emulsan, was prepared in deionized water and heated to 50-60 C. while continuously stirring. The pH of the suspension was adjusted to pH 8.5 by adding 50% by weight sodium hydroxide (diluted, if necessary). Protease enzyme (NOVO Industries, 1.5M Alcalase) was added at a level of 1 part protease:500 parts solid @-emulsan. The mixture was allowed to remain at 50-60 C. while being stirred for about three hours. Reactions were run to completion as judged by the absence of visible precipitable @-emulsans following centrifugation of the reaction mixture. After completion of the enzyme treatment, the reaction mixtures were raised to approximately 70 C. to denature the protease and stop its activity. The solutions were cooled to room temperature and Cosan PMA-30 (Cosan Corporation), a preservative, was added at a level of 1 part Cosan:500 parts @-emulsan solution.

By another method, enzyme treatment of the @-emulsans was performed prior to drum drying according to the following protocol. Fermentation broth containing @-emulsans resulting from a fermentation of *Acinetobacter calcoaceticus* ATCC 31012 in ethanol medium was centrifuged to remove approximately 90% of the bacterial cells. To the centrifuged broth, protease enzyme (as previously described) was added in a ratio of 1 gram protease:500 units per milligram of Specific Emulsification Activity (where one unit per milligram of Specific Emulsification Activity is defined as that amount of emulsifying activity per milligram of bioemulsifier which yields 100 Klett absorption units using a standard hydrocarbon mixture consisting of 0.1 ml of 1:1 (v/v) hexadecane/2-methylnaphthalene and 7.5 ml of Tris-Magnesium buffer). The protease reaction was run to completion as described supra. The protease-treated centrifuged broth was then evaporated to a 10% (w/v) slurry of @-emulsans. The slurry was sprayed dried and the resulting material is also referred to as technical grade @-emulsan.

Bar soaps were formulated with @-emulsans prepared by each of the foregoing procedures. The method of preparation of @-emulsans made no apparent difference in the final bar soap product, as evaluated in the laboratory on the basis of a qualitative criterion, feel to the hands. The @-emulsans prepared by the second procedure described supra were used in the personal care products distributed to individuals to be evaluated as personal skin and hair care products and as beneficial agents for such skin conditions as acne, psoriasis, eczema, dandruff, etc.

6.2. EMULSAN FORMULATION FOR USE IN SOAPS AND SHAMPOOS

The @-emulsans prepared by the methods described in Section 6.1. were not added directly to the soap bases described in Section 6.3.1. although they can be. Instead, the @-emulsans were first formulated into a composition comprising non-ionic surfactants and water. The formula for the composition was the following: 30% Triton X-114 (an ethoxylated alkyphenol commercially available from Rohm & Haas Co., Philadelphia, PA); 10% Tergitol TMN-6 (an ethoxylated alcohol commercially available from Union Carbide Corp., Danbury, CT); 3% @-emulsan; and 57% water. (Percentages are on a weight basis). Also, this formulation was added to the shampoo bases set forth in Tables II and III in Section 6.5.1. Shampoos containing the formulation were used in the shampoo testing reported in Section 6.5.2. However, the subjects of Sections 6.6, 6.7 and 6.8 used shampoos to which @-emulsan had been added directly.

6.3. EMULSAN IN TOILET SOAP

6.3.1. BAR SOAP COMPOSITION

Standard toilet soap base (Steinfels, Switzerland) was used which contained, approximately, 10% coconut oil; 40% beef tallow; and 50% pork grease. A superfatted soap base was also used. The formulation described in Section 6.2 was readily incorporated together with color and perfume (Firmenich S.A., Switzerland) by intensive mixing on a three-roller mill and final extrusion in a laboratory soap plodder. The final concentration of @-emulsan in the bar soap ranged from 0.05% to 0.3% on a weight basis. At these low concentrations, there was no detectable odor of @-emulsan. The use of concentrations of @-emulsan higher than 0.3% resulted in soap bars that left a dry feeling to the skin after washing. This drying effect is probably due to the presence of the synthetic detergents in the formulation added to the soap bases. (See Section 6.2., supra.)

6.3.2. BAR SOAP TESTING

A group of ten panelists were given soap bars with and without @-emulsan as an ingredient. The concentration of @-emulsan in soap bars containing the bioemulsifier was 0.15% by weight. Each panelist alternated soap bars on a daily basis, one day using the soap bar containing @-emulsan and the next day using the control soap bar without @-emulsan. The panelists were asked to evaluate and compare the soap bars based on several qualitative, subjective criteria, including foam formation on hands, foam consistency, feeling on wet skin and feeling on dry skin. No special soil was applied to the panelists' hands.

The panelists reported that there was no significant difference in foaming properties of the soap bars, although the @-emulsan-containing soap bars lathered into a perceptibly creamier feeling foam. Also, seven out of ten panelists indicated their skin had a better, creamier feeling after washing with the @-emulsan-containing soap bars.

6.4. EFFECT OF EMULSAN-CONTAINING SOAP BARS ON SKIN CONDITIONS

6.4.1. EFFECT OF EMULSAN-CONTAINING SOAP BARS ON ACNE

Several individuals with acne and acne-like conditions (e.g., blemishes, pimples and the like) washed the affected parts of their bodies with @-emulsan-containing bar soap for varying periods of time and experienced certain beneficial effects as the result of such use. Individual cases are presented as follows:

One subject was a teenage female who had a moderately severe acne-like condition on her back. The condition had not been medically diagnosed and is therefore referred to as an "acne-like" condition. The condition had been present for about one year during which time the subject had used various cleansers on her back. The use of @-emulsan-containing bar soap (0.15% w/v technical grade @-emulsan) on a daily basis during bathing coincided with the prompt, gradual disappearance of the subject's acne-like condition. In less than one week, the acne-like condition was gone. When the supply of @-emulsion-containing soap was exhausted, the condition returned. The subject was given another supply of @-emulsan-containing bar soap (0.05% w/v technical grade @-emulsan) and again the acne-like condition went away upon daily use of the soap. The subject also noted that the soap left her skin feeling smooth.

Another subject was a teenage male with a medically-diagnosed severe case of acne on his face and back. The acne had been present for about one to two years during which time the subject had used various cleansers on his face and back. The use of @-emulsan-containing bar soap (0.15% w/v technical grade @-emulsan) on a daily basis during bathing coincided with a prompt and gradual improvement of the acne on the subject's face and back. In approximately one week, the condition had changed from a severe to a slight case of acne; this improvement was noted by a physician.

Another subject was a teenage female who had a moderately severe acne-like condition (not medically diagnosed) on her face. The condition had been present for several months during which time the subject had used various cleansers on her face. The use of @-emulsan-containing bar soap (0.05% w/v technical grade @-emulsan) on a daily basis during bathing coincided with a noticeable improvement in the acne-like condition. In less than one week, the acne-like condition changed from moderate to very slight. The subject further noted that the soap left her skin feeling smooth.

Another subject was a male in his early twenties with a moderately severe acne-like condition (not medically diagnosed) on his face and chest. The condition had been present for several years. Upon daily washings of the affected body parts with @-emulsan-containing bar soap (0.18% w/v technical grade @-emulsan), the subject experienced the following results. The acne-like condition on the chest improved significantly within 3 days and cleared up completely within two weeks of use. With regard to the acne-like condition on the face, the subject observed a flare-up of the condition within the first week of use. A stinging sensation upon washing was also experienced. Thereafter, upon continued use of the soap, the acne-like condition on the subject's face completely disappeared within 7 days.

Another subject was a teenage female who had a moderate amount of persistent blemishes on her face. Various medications had been tried with little success; the problem persisted. Then the subject began to use a bar of @-emulsan-containing soap (0.18% w/v technical grade @-emulsan) on a daily basis. An improvement in the condition was noticed in seven days. The subject's complexion had cleared up by the end of the two weeks and remained clear as long as the soap was used. After discontinuance of use of the bar soap, the blemishes gradually began to reappear.

Another subject was a twenty-one year old male with mild to moderate acne on the lower face, chin and upper neck. The subject washed his face daily with @-emulsan containing bar soap (0.18% w/v technical grade @-emulsan). A definite improvement was noticed after three to four weeks of use. The condition returned after the supply of @-emulsan-containing bar soap was exhausted (after about eight to ten weeks).

6.4.2. EFFECT OF EMULSAN-CONTAINING SOAP-BARS ON RAZOR BURN

The subjects were two adult males with intermittent yet severe cases of razor burn on their necks. Use of an @-emulsan-containing bar soap (0.05% w/v technical grade @-emulsan) for showering immediately prior to shaving significantly reduced the incidence of razor burn. Results were immediately observed after use of the bar soap. Any razor burn experienced was very slight.

6.5. EMULSAN IN SHAMPOO

6.5.1. SHAMPOO BASE COMPOSITIONS

Emulsan shampoos were formulated by adding 0.1–0.20% @-emulsan to three shampoo base compositions developed for use with the technical grade @-emulsans described in Section 6.1. Formulas for the shampoo bases, designated DAM 82/25 and DAM 83/12, are presented in Tables II and III, respectively. The formula for the third complete shampoo composition (i.e., including @-emulsan), designated PFC 124105 is presented in Table IV. Trade names and suppliers of commercially available products are also provided.

TABLE II

COMPOSITION OF SHAMPOO BASE DAM 82/25

| Ingredient | Percent | Commercial Product and Supplier |
|---|---|---|
| Glycol distearate | 0.5 | Genapol PMS, Hoechst Laboratories (Puteaux, France) |
| Cocamide Diethanolamide | 2.5 | Comperlan KD, Henkel Corp. (Dusseldorf, West Germany) |
| Sodium laureth sulfate | 21.0 | Texapon N 25, Henkel Corporation |
| Demineralized water | 44.3 | |
| Methylchloroisothiazol-inone and methylisothiazolinone | 0.1 | Kathon CG, Rohm & Haas Co. (Philadelphia, PA) |
| Citric acid | 0.1 | |
| Sodium chloride | 0.5 | |
| Sodium lauroyl sarcosinate | 5.0 | Medialan LD, Hoechst Laboratories |
| Polyethylene glycol-15 tallow polyamine | 1.0 | Polyquart H, Henkel Corp. |
| Hydrolyzed animal protein | 4.0 | Nutrilan L Liquid, Grunau (Bavaria, West Germany) |
| Cocoamphocarboxy-glycinate/Sodium laureth sulfate/Sodium lauryl sulfate | 20.0 | Amphotensid 9M, Zschimmer & Schwartz GMBH & Co. (Lahnstein, West Germany) |
| Perfume | 1.0 | Firmenich S.A. (Geneva, Switzerland) |

TABLE III

COMPOSITION OF SHAMPOO BASE DAM 83/12

| Ingredient | Percent | Commercial Product and Supplier |
|---|---|---|
| Citric acid | 0.2 | |
| Methylchloroisothiazol-inone and methylisothiazolinone | 0.1 | Kathon CG, Rohm & Haas Co. (Philadelphia, PA) |
| Water | 45.7 | |
| Sorbitol 70% | 5.0 | |
| Polyethylene glycol alkyl ether 60% | 15.0 | Triton CB 110, Rohm & Haas Co. |
| Cocoamphocarboxy-glycinate/sodium laureth sulfate/Sodium lauryl sulfate | 30.0 | Amphotensid 9M, Zschimmer & Schwarz GMBH & Co. (Lahnstein, West Germany) |
| Cocamide Diethanolamide | 3.0 | Comperlan KD, Henkel Corp. (Dusseldorf, West Germany) |
| Pearly agent | 0.5 | Product GM 4055, Zschimmer & Schwarz GMBH & Co. |
| Perfume | 0.5 | Firmenich S.A. (Geneva, Switzerland) |

TABLE IV

COMPOSITION OF SHAMPOO PFC 124105

| Ingredient | Percent | Commercial Product and Supplier |
|---|---|---|
| Sodium Lauryl Ether (POE 2) Sulfate | 21.0 | Sipon ES-2, Alcolac, Inc. (Baltimore, MD) |
| Ethylene Glycol Distearate | 0.5 | Genapol/PMS, Hoechst Laboratories (Puteaux, France) |
| Coconut Diethanolamide | 2.5 | Comperlan KD, Henkel Corp. (Dusseldorf, West Germany) |
| Water | 44.2 | |
| Technical @-Emulsan | 0.2 | Emulsan, Petroferm USA, Inc. (Amelia Island, FL) |
| Preservative | 0.1 | Kathon CG, Rohm & Haas Co. (Philadelphia, PA) |
| Citric Acid | 0.2 | Fisher Scientific Co. (Pittsburgh, PA) |
| Sodium Chloride | 0.5 | Baker Chemical Co. (Phillipsburg, NJ) |
| Sodium Lauroyl Sarcosinate | 5.0 | Hamposyl L-30, Hampshire (Nashua, NH) |
| Polyglycol Polyamine Condensate | 1.0 | Polyquart H, Henkel Corp. (Dusseldorf, West Germany) |
| Hydrolyzed Animal Protein | 4.0 | Polypeptide 37, Inolex Chemical Co. (Philadelphia, PA) |
| Coco Amphocarboxy Glycinate | 20.0 | Monateric CDL, Mona Industries, Inc. (Paterson, NJ) |
| Fragrance | 0.8 | 72.175, Firmenich S.A. (Geneva, Switzerland) |

DAM 82/25 was prepared in the following manner. The glycol distearate, cocamide diethanolamide and sodium laureth sulfate were heated to approximately 65–70 C and mixed until homogeneous; this mixture is referred to as Part A. The remaining ingredients, except for the perfume, were combined to make a mixture referred to as Part B. Slowly, a little at a time, Part B was added into Part A, while mixing, until the combined Parts A and B were perfectly homogeneous. Finally, the perfume was added. DAM 83/12 was prepared by mixing all the ingredients listed in Table III, one after the other, according to the sequence of ingredients listed.

PFC 124105 was prepared in the following manner. The sodium lauryl ether (POE 2) sulfate, ethylene glycol distearate and the coconut diethanolamide were heated to approximately 60° C. and stirred until homogeneous; this mixture is referred to as Part A. As a separate mixture, the @-emulsan is dissolved in water to which the citric acid and sodium chloride are then added and stirred until dissolved. Next, the remaining ingredients of Table IV are added to the @-emulsan, citric acid and sodium chloride solution. This mixture is stirred until homogeneous and is referred to as Part B. Slowly, mixture B is added to mixture A while stirring continuously. The pH of the final combined mixture is checked and is adjusted to pH 6–7 with either citric acid or sodium hydroxide, as necessary.

6.5.2. SHAMPOO TESTING

Shampoo (DAM 82/25) containing technical grade @-emulsan at concentrations in the range of approximately 0.1–0.15% yielded the best results. Higher concentrations of this material made hair dull and unpleasant to touch.

The @-emulsan shampoo was used to wash hair containing large amounts of residues from fixative agents such as laquers, creams, hair sprays, etc. Hair containing such residues is normally difficult to wash; other shampoos leave fine white residues that adhere to combs when the hair is combed after washing. It was found that the addition of 0.15% technical grade @-emulsan to the composition designated DAM/25, described in section 6.5.1 resulted in a shampoo with better cleaning power for the previously mentioned residues. Furthermore, no white residues were observed on combs after combing hair that had been washed with the @-emulsan shampoo.

Hair washed with the @-emulsan shampoo was evaluated with regard to regreasing, i.e., the length of the time interval before washing was again required. For some test persons the interval between washings was 30% longer than normal; for others, the interval between washing was twice as long as normal.

The @-emulsan shampoo was further evaluated on hair of varying thicknesses. It was observed that the shampoo imparted a slight fixative effect to fine hair. On the other hand, it was observed that the shampoo had a tendency to leave thick hair harsh and unpleasant to touch at @-emulsan concentrations higher than about 0.2%.

6.6. EFFECT OF EMULSAN-CONTAINING SHAMPOO ON SCALP CONDITIONS

6.6.1. EFFECT OF EMULSAN-CONTAINING SHAMPOO ON DANDRUFF

The subject was an adult male with a moderately severe case of dandruff that had persisted for several years. The subject had never consulted a physician about his dandruff condition but had been using various commercially available medicated shampoos on his hair and scalp. In approximately one week during which the subject used DAM 82/25 shampoo containing 0.15% technical grade @-emulsan, an improvement in the condition was observed. Upon further use the dandruff had disappeared. When the supply of shampoo was exhausted, the dandruff condition returned to its former level. Resumption of use of the @-emulsan shampoo again resulted in an improvement in the condition. The subject also observed that his hair was better conditioned after having used the @-emulsan shampoo.

6.6.2. EFFECT OF EMULSAN-CONTAINING SHAMPOO ON ECZEMA/PSORIASIS OF THE SCALP

The subject was an adult female with a moderate form of an eczema/psoriasis-like condition on her scalp. The condition had been medically diagnosed. This skin condition, which had been present for several years and which had been kept marginally controlled by treatments, e.g., medicated shampoos, prescribed by dermatologists, was observed to be significantly improved upon use of the @-emulsan shampoo (DAM 82/25). Results were observed in approximately one week with shampoo containing 0.18% technical grade @-emulsan. When the supply of shampoo was exhausted, the skin condition returned to its former state. Unbeknownst to her, the subject was next given a placebo shampoo which did not contain any @-emulsan. Within a few days, the subject, of her own initiative, reported that she was no longer observing the same beneficial effects as she had with the initial supply. The subject was then provided with a standard store-bought brand of baby shampoo to which 0.175% technical grade @-emulsan was added. Use of this shampoo resulted in significant improvement of the condition. This subject also observed that emulsan-containing shampoos left her hair feeling better conditioned.

6.7. CONDITIONING EFFECTS OF EMULSAN-CONTAINING SHAMPOO

6.7.1. DECREASED STATIC BUILD-UP

The subject was an adult male who experienced static build-up in his hair when blow drying it after shampooing with conventional shampoos. The first time the subject used @-emulsan shampoo (DAM 82/25 containing 0.15% technical grade @-emulsan), he observed a very noticeable loss of static in his hair after blow drying. Static returned when shampoos without @-emulsan were used. Resumption of use of @-emulsan shampoo again eliminated the static build-up.

6.7.2. IMPROVED SHINE

The subject was an adult female who normally experienced dullness of her hair after shampooing with conventional shampoos. However, a very noticeable improvement in "shine" was observed each time @-emulsan shampoo (0 15% technical grade @-emulsan in DAM 82/25) was used. The @-emulsan shampoo was used over a period of approximately nine months during which time the improved "shine" was continually observed.

6.8 EFFECT OF EMULSAN-CONTAINING SHAMPOO ON MILDEW

During a period of use of emulsan-containing shampoo (0.15% technical grade @-emulsan in DAM 82/25), mildew did not accumulate on the shower curtain. When the shampoo supply was exhausted, the mildew began to reappear on the shower curtain. Resumption of use of emulsan shampoo upon obtaining a new supply gave a gradual decrease in mildew severity.

6.9. EMULSAN IN CLEANSING CREAMS AND LOTIONS

6.9.1. CLEANSING CREAM AND LOTION COMPOSITIONS

Emulsan-containing cleansing creams and lotions were formulated by adding 0.2% technical grade @-emulsan (as described in Section 6.1) to two different formulations. These composition, designated Cosform 11 and Cosform 30, are presented in Tables V and VI, respectively.

TABLE V

| COMPOSITION OF COSFORM 11 | | |
|---|---|---|
| Ingredient | Percent | Commercial Product and Supplier |
| PEG 400 Monostearate | 3.6 | Kessco PCG 400 Monostearate, Stepan Co. (Northfield, IL) |
| Mineral Oil | 1.0 | |
| Glycerol Monostearate | 10.0 | Kessco Glycerol Monostearate S.E., Stepan Co. (Northfield, IL) |
| Propyl Paraben | 0.1 | Lexgard P, Inolex Chemical Co. (Philadelphia, PA) |
| Methyl Paraben | 0.1 | Lexgard M, Inolex Chemical Co. (Philadelphia, PA) |
| Perfume | q.s. | Firmenich S.A. (Geneva, Switzerland) |
| Propylene Glycol | 6.0 | Apperson Chem. (Jacksonville, FL) |
| Technical @-Emulsan | 0.2 | Emulsan, Petroferm USA, Inc. (Amelia Island, FL) |
| Water | 79.0 | |

Cosform 11 was prepared in the following manner. Technical grade @-emulsan was dissolved in water to which propylene glycol was then added, with agitation. This mixture is referred to as Part C. Part C was heated to approximately 75 C. The PEG 400 monostearate, mineral oil, glycerol monostearate, propyl paraben and methyl paraben were combined in a mixture referred to as Part A. Part A was heated to approximately 70° C. The heated Part C was added to the heated Part A with agitation. The combination of Parts A and C were mixed thoroughly and allowed to cool. When this combination of Parts A and C reached approximately 40° C., the perfume (Part B) was added and mixed thoroughly. The final composition can be packaged as desired.

TABLE VI

COMPOSITION OF COSFORM 30

| Ingredient | Percent | Commercial Product and Supplier |
|---|---|---|
| PEG 400 Monostearate | 3.6 | Kessco PEG 400 Monostearate, Stepan Co. (Northfield, IL) |
| Aloe Extract | 1.0 | FFP #104, Florida Food Products (Jacksonville, FL) |
| Glycerol Monostearate | 10.0 | Kessco Glycerol Monostearates S.E., Stepan Co. (Northfield, IL) |
| Propyl Paraben | 0.1 | Lexgard P, Inolex Chemical Co. (Philadelphia, PA) |
| Methyl Paraben | 0.1 | Lexgard M, Inolex Chemical Co. (Philadelphia, PA) |
| Propylene Glycol | 6.0 | Apperson Chem. (Jacksonville, FL) |
| Water | 78.5 | |
| Technical @-Emulsan | 0.2 | Emulsan, Petroferm USA, Inc. (Amelia Island, FL) |
| Mucopolysaccharide | 0.5 | Mucopolysaccharide I, Centerchem, Inc. (Tarrytown, NY) |

Cosform 30 was prepared in the following manner. Technical grade @-emulsan was dissolved in water to which the mucopolysaccharide was then added and dissolved. To this solution, the propylene glycol was added and dissolved. This mixture is referred to as Part B. The remaining ingredients, PEG 400 monostearate, aloe extract, glycerol monostearate, propyl paraben and methyl paraben, were combined as a mixture referred to as Part A. Both Part A and Part B were heated to approximately 75° C. The heated mixtures were combined with agitation. Stirring was continued while the final combined composition cooled. The composition was packaged at approximately 40° C.

6.9.2. EFFECT OF EMULSAN-CONTAINING CLEANSING CREAMS AND LOTIONS ON ACNE AND OILY SKIN

Several individuals with acne and acne-like conditions washed the affected parts of their bodies with the @-emulsan-containing Cosform 11 and Cosform 30 formulations set forth in Section 6.9.1. for varying periods of time and experienced certain beneficial effects as the result of such use. For the most part, the formulations were applied as cleansers, i.e., they were rinsed off during washing. The formulations can also be used as a topical agent, applied to the skin without rinsing off. Individual cases are presented as follows.

One subject was a twenty-three year old male with blemishes on his face. Cosform 11 was used twice a day, every other day, over a twenty day period as a cleanser. Daily use was initially tried but such use tended to leave the skin overly dry. Hence the subject switched to an every other day regime. Favorable results were detected by the subject within one day of use. At the end of the trial period, an improvement was noted by the subject who found Cosform 11 to be more effective against his blemishes than the commercially available products Oxy-10, Clearasil and Stridex which he had tried in the past.

Another subject was a sixteen year old male with acne on his face and back. Cosform 11 was used as a cleanser twice daily on the affected areas for a period of several days. Improvement was noticed by the subject within one day of use. The subject had used the commercially available product De-Squaman X previously and found Cosform 11 to be more effective against his acne.

Another subject was a twenty-three year old female with oily skin and some blemishes. Cosform 30 was used as a cleanser over a three week period. Cosform 30 was applied to the skin each morning and rinsed off with warm water. Results were obtained by the subject within two to three days. The subject noted that her skin was not as oily as it had been prior to the use of Cosform 30 and that her blemishes had cleared up noticeably.

Another subject was a nineteen year old male with oily skin and occasional blemishes. Cosform 30 was used as a cleanser twice daily for a period of a month. The subject applied Cosform 30 to the face, let it remain for a few minutes, and then rinsed. The subject reported that he noticed results within three weeks. His skin was no longer oily; it was smooth and blemish-free. During the test period rubbing alcohol had also been used.

Another subject was a teenage female who had a moderate amount of acne on her face prior to the use of @-emulsan-containing soap. When she stopped using the soap, the acne returned. When she used Cosform 11, and later Cosform 30, twice daily, the acne went away after seven to ten days.

During the course of her use of Cosform 30, the same teenage female described above was supplied with a Cosform 30 placebo (identical to the active Cosform 30 except for the absence of @-emulsan), without being told of the switch. After approximately one week she reported the placebo to be substantially ineffective in controlling her acne. She was supplied with an active sample of Cosform 30 and her acne was again brought under control within a few days.

A teenage male subject who had been using tetracycline to treat severe acne on his face was supplied with Cosform 30. The tetracycline alone was only marginally effective in controlling his condition. Use of Cosform 30 together with tetracycline gave (after approximately one week) significantly better results than tetracycline alone. Interrupting tetracycline treatment while continuing the use of Cosform 30 resulted in reappearance of a mild acne problem, which disappeared again approximately ten days after resumption of tetracycline therapy.

6.9.3. EFFECT OF EMULSAN-CONTAINING CLEANSING CREAMS AND LOTIONS ON NORMAL SKIN

Several subjects, male and female, with normal skin have used either Cosform 11 or Cosform 30 as cleansers, i.e., applying it to facial skin and rinsing it off with water, on a daily or twice daily basis for trial periods of one to two weeks. Each reported that within a period of four days they found the product effective at leaving their skin feeling soft and smooth.

6.10. EMULSAN IN MOISTURIZING CREAMS AND LOTIONS

6.10.1. MOISTURIZER COMPOSITIONS

The @-emulsan-containing formulation Cosform 30 can be used as a moisturizer as well as a cleanser. In addition to Cosform 30, three other moisturizer formulations have been devised containing technical grade @-emulsan as a moisturizing and feel improving agent. The compositions of these moisturizers, designated Cosform 25, Cosform 18b and Cosform 27 are set forth in Tables VII, VIII and IX, respectively.

TABLE VII
COMPOSITION OF COSFORM 25

| Ingredient | Percent | Commercial Product and Supplier |
|---|---|---|
| Aloe Oil | 10.0 | FFP #104, Florida Food Products (Jacksonville, FL) |
| Stearic Acid | 3.0 | Aldrich Chemical Co. (Milwaukee, WI) |
| Synthetic Spermaceti Wax | 2.0 | Crodamol SS, Croda, Inc. (New York, NY) |
| Cetyl Alcohol (Hexadecanol) | 1.0 | Aldrich Chemical Co. (Milwaukee, WI) |
| Isopropyl Myristate | 3.0 | Crodamol IPM, Croda, Inc. (New York, NY) |
| Glycerol | 4.0 | Emery 916, Emery Industries (Cincinnati, OH) |
| Water | 75.2 | |
| Technical @-Emulsan | 0.2 | Emulsan, Petroferm USA, Inc. (Amelia Island, FL) |
| Triethanolamine | 0.9 | Florida Solvents (Jacksonville, FL) |
| Mucopolysaccharide | 0.5 | Mucopolysaccharide I, Centerchem, Inc. (Tarrytown, NY) |
| Preservative | 0.2 | Kathon CG, Rohm & Haas Co. (Philadelphia, PA) |

Cosform 25 was prepared in the following manner. Technical grade @-emulsan was dissolved in water. To this solution, glycerol, mucopolysaccharide and triethanolamine were added and allowed to dissolve. The resulting mixture is referred to as Part B. The aloe oil, stearic acid, synthetic spermaceti wax, cetyl alcohol and isopropyl myristate were combined to form a mixture referred to as Part A, which was heated to approximately 70° C. Part B was also heated to approximately 70° C. The heated Parts A and B were combined with mixing and were continuously stirred while the mixture cooled. When the temperature of the combined mixture of Parts A and B had reached approximately 40° C., the Kathon CG was added with thorough mixing. The final mixture can be packaged while still warm.

TABLE VIII
COMPOSITION OF COSFORM 18b

| Ingredient | Percent | Commercial Product and Supplier |
|---|---|---|
| Aloe Oil | 10.0 | FFP #104, Florida Food Products (Jacksonville, FL) |
| Stearic Acid | 3.0 | Aldrich Chemical Co. (Milwaukee, WI) |
| Synthetic Spermaceti Wax | 2.0 | Crodamol SS, Croda, Inc. (New York, NY) |
| Cetyl Alcohol (Hexadecanol) | 1.0 | Aldrich Chemical Co. (Milwaukee, WI) |
| Isopropyl Myristate | 3.0 | Crodamol IPM, Croda, Inc. (New York, NY) |
| Glycerol | 4.0 | Emery 916, Emery Industries (Cincinnati, OH) |
| Water | 75.7 | |
| Technical @-Emulsan | 0.2 | Emulsan, Petroferm USA, Inc. (Amelia Island, FL) |
| Triethanolamine | 0.9 | Florida Solvents (Jacksonville, FL) |
| Preservative | 0.2 | Kathon CG, Rohm & Haas Co. (Philadelphia, PA) |

Cosform 18b was prepared in the following manner. Technical grade @-emulsan was dissolved in water to which the glycerol and triethanolamine was then added and allowed to dissolve. This mixture is referred to as Part B. The aloe oil, stearic acid, synthetic spermaceti wax, cetyl alcohol and isopropyl myristate were combined in a mixture referred to as Part A. Part B was heated to approximately 70° C. and stirred until uniform. Part A was also heated to approximately 70° C. The heated Part B was added to heated Part A and mixed vigorously. The resulting mixture was stirred continuously while cooling. When the temperature of this mixture reached approximately 40° C., the Kathon CG was added and mixed thoroughly with stirring. The final composition was packaged at 40° C.

TABLE IX
COMPOSITION OF COSFORM 27

| Ingredient | Percent | Commercial Product and Supplier |
|---|---|---|
| Aloe Oil | 10.0 | FFP #104, Florida Food Products (Jacksonville, FL) |
| Stearic Acid | 3.0 | Aldrich Chemical Co. (Milwaukee, WI) |
| Synthetic Spermaceti Wax | 2.0 | Crodamol SS, Croda Inc. (New York, NY) |
| Cetyl Alcohol (Hexadecanol) | 1.0 | Aldrich Chemical Co. (Milwaukee, WI) |
| Isopropyl Myristate | 3.0 | Crodamol IPM, Croda Inc. (New York, NY) |
| Glycerol | 4.0 | Emery 916 Emery Industries (Cincinnati, OH) |
| Water | 70.2 | |
| Technical @-Emulsan | 0.2 | Emulsan, Petroferm USA, Inc. (Amelia Island, FL) |
| Triethanolamine | 0.9 | Florida Solvents (Jacksonville, FL) |
| Eflaplant Chamomile | 2.5 | Eflaplant, Flachsmann AG (Zurich, Switzerland) |
| Eflaplant Hayflower | 2.5 | Eflaplant, Flachsmann AG (Zurich, Switzerland) |
| Mucopolysaccharide | 0.5 | Mucopolysaccharide I, Centerchem, Inc. (Tarrytown, NY) |
| Preservative | 0.1 | Lexgard M, Inolex Chemical Co. (Philadelphia, PA) |
| Preservative | 0.1 | Lexgard P, Inolex Chemical Co. |

TABLE IX-continued

COMPOSITION OF COSFORM 27

| Ingredient | Percent | Commercial Product and Supplier |
|---|---|---|
| | | (Philadelphia, PA) |

Cosform 27 was prepared in the following manner. The aloe oil, stearic acid, synthetic spermaceti wax, cetyl alcohol and isopropyl myristate were combined and heated to approximately 70° C. This mixture is referred to as Part A. Technical @-emulsan was dissolved in water to which the glycerol, triethanolamine, eflaplant chamomile, eflaplant hayflower and mucopolysaccharide were added and dissolved. This mixture, referred to as Part B, was heated while stirring to approximately 70° C. The heated Parts A and B were combined and mixed vigorously. Mixing continued while cooling. Lexgard M and Lexgard P were added to the mixture of Parts A and B when such mixture had cooled to about 40° C. The final composition was mixed thoroughly and was packaged while it was still at approximately 40° C.

6.10.2. EFFECT OF EMULSAN-CONTAINING MOISTURIZERS ON SKIN

The Cosform 30 composition set forth in Section 6.9.1 was tested, along with three modified forms of Cosform 30, as a moisturizer by a panel of twelve subjects. The regular Cosform 30 formulation contains both @-emulsan and mucopolysaccharide. Three modified forms of Cosform 30 were prepared, one without emulsan but with mucopolysaccharide, another with emulsan but without mucopolysaccharide and yet another without either emulsan or mucopolysaccharide.

Each of twelve subjects compared two formulations (of unknown composition to the subject as well as to the test supervisor) by rubbing it in on the back of the hand (one sample per hand), rinsing off with water, and drying. The subjects were asked to give their preference (typically based upon smooth, non-greasy feel) after drying. The results are presented in Table X, in which "X" indicates which products were compared and "X*" indicates preference.

TABLE X
SCREENING OF COSFORM 30 AS MOISTURIZER

| Subject # | #1 | #2 | #3 | #4 |
|---|---|---|---|---|
| 1 | X | X | | |
| 2 | X* | | X | |
| 3 | X* | | | X |
| 4 | | X | X* | |
| 5 | | X | | X* |
| 6 | | | X | X |
| 7 | X* | X | | |
| 8 | X | | X* | |
| 9 | X* | | | X |
| 10 | | X | X* | |
| 11 | | X* | | X |
| 12 | | | X | X |
| Incidents of Preference (maximum 6) | 4/6 | 1/6 | 3/6 | 1/6 |
| No preference | | | | 3/12 |

Key to Samples:
1: Cosform 30 w/emulsan and w/mucopolysaccharide
2: Cosform 30 w/o emulsan and w/mucopolysaccharide
3: Cosform 30 w/emulsan and w/o mucopolysaccharide
4: Cosform 30 w/o emulsan and w/o mucopolysaccharide The results of this test indicate that samples containing emulsan are preferred, 7:2, over samples not containing emulsan. Furthermore, in every case in which a preference was expressed and in which an emulsan-containing sample was compared directly against a sample without emulsan, the subject preferred the emulsan-containing sample. (Subject Nos. 3, 4, 7, 9 and 10).

Several individuals have evaluated Cosform 25 and Cosform 18b as moisturizers. Individual cases are presented as follows.

One subject was a forty-five year old woman who used Cosform 25 over a two month period, alternating it with Cosform 18b during the first four weeks. The products were used daily, in the morning and night as a cleanser and also in the morning as an under make-up moisturizer. The subject reported that results were observed immediately. Both products left the subject's facial skin feeling very soft and smooth.

Another subject was a twenty-five year old female who used Cosform 18b for a period of about a month and a half on a daily basis. The Cosform 18b was used both as a facial cleanser and a moisturizer. The subject reported that she felt as though water had been added to her skin, leaving her skin feeling soft and smooth.

Another subject was a thirty-nine year old female who used Cosform 25 for a month. She applied Cosform 25 nightly as a moisturizer after cleaning her face. The subject reported that at the end of the one-month period her facial wrinkles were not as pronounced.

Another subject was a twenty-nine year old female who used Cosform 25 for a one-month period. The product was used daily as a cleanser. The subject reported that results were observed within four to five days. Her skin was smooth and had cleared up.

Another subject was a fourteen year old female with some pimples on her face. She used Cosform 18b for five weeks, twice daily. She washed her face with her usual soap and applied Cosform 18b after washing. According to the subject, results were observed within three days. She had less pimples and her skin was smooth and soft.

6.11. EMULSAN IN MUD MASK

A mud mask formulation, Cosform 16, was prepared and upon used by two test subjects was judged to give excellent performance. The formulation is presented in Table XI.

TABLE XI
COMPOSITION OF COSFORM 16

| Ingredient | Percent | Commercial Product and Supplier |
|---|---|---|
| A | | |
| Diatomaceous Earth | 3.5 | Celite S12, Manville Corp. (Denver, CO) |
| Bentonite | 6.9 | Accofloc 350, American Colloid Co. (Skokie, IL) |
| Water | 41.5 | |
| Technical @-Emulsan | 0.2 | Emulsan, Petroferm USA, Inc. (Amelia Island, FL) |
| B | | |
| Gelatin | 0.5 | |
| Water | 9.9 | |
| C | | |
| Fumed Silica | 2.6 | Aerosil 200, Degussa Corp., (Teterboro, NJ) |
| Water | 23.6 | |
| D | | |
| Glycerol Monostearate | 1.9 | Kessco PEG 400 Monostearate, Stepan |

TABLE XI-continued

COMPOSITION OF COSFORM 16

| Ingredient | Percent | Commercial Product and Supplier |
|---|---|---|
| | | Co. (Northfield, IL) |
| Ethyl Alcohol | 5.2 | Fisher Scientific Co. (Pittsburgh, PA) |
| Oleth 10 | 2.1 | Volpo 10, Croda, Inc. (New York, NY) |
| Sodium Isostearoyl Lactylate | 0.6 | Pationic ISL, Rita/ Patco Products (Kansas City, MO) |
| Sodium Laureth-12 Sulfate | 1.3 | Standapol 130-E, Henkel Corp. (Dusseldorf, W. Germany) |
| Preservative | 0.1 | Lexgard M, Inolex Chemical Co. (Philadelphia, PA) |
| Preservative | 0.1 | Lexgard P, Inolex Chemical Co. (Philadelphia, PA) |

Cosform 16 was prepared as follows. Accofloc 350 Celite and technical grade @-emulsan were dispersed in water with vigorous and complete mixing, yielding a mixture referred to as Part A. The water of Part B (see Table XI) was heated to boiling and was added to the gelatin with mixing. The resulting Part B mixture was chilled until firm. Part B was added to Part A and mixed well. The water of Part C was added to Aerosil 200 and mixed well. The glycerol monostearate was dissolved in hot ethanol and then the remaining Part D (see Table XI) ingredients were added together with Parts C, B and A. The final combined mixture was warmed and stirred thoroughly and then homogenized. Cosform 16 was packaged while still warm.

It is apparent that many modifications and variations of this invention as hereinabove set forth may be made without departing from the spirit and scope thereof. The specific embodiments described are given by way of example only and the invention is limited only by the terms of the appended claims. The invention described and claimed herein is not to be limited in scope by the bacterial cell lines deposited, since the deposited embodiments are intended as illustrations of an aspect of the invention and any equivalent cell lines which produce functionally equivalent agents are within the scope of this invention.

What is claimed is:

1. In a moisturizing cream or lotion for topical application to skin or scalp, the improvement which comprises incorporation in such moisturizing cream or lotion at least about 0.02% by weight of a bioemulsifier produced by an *Acinetobacter calcoaceticus* species, which bioemulsifier is characterized by (a) a specific emulsification Activity of at least about 25 units per milligram; (b) the ability to remove sebum; and (c) the ability to interfere with microbial adhesion on skin or hair.

2. The moisturizing cream or lotion according to claim 1 in which the *Acinetobacter calcoaceticus* is selected from the group consisting of *Acinetobacter calcoaceticus* ATCC 31012, *Acinetobacter calcoaceticus* NRRL B-15616, *Acinetobacter calcoaceticus* NRRL B-15847, *Acinetobacter calcoaceticus* NRRL B-15848, *Acinetobacter calcoaceticus* NRRL B-15849, *Acinetobacter calcoaceticus* NRRL B-15850, and *Acinetobacter calcoaceticus* NRRL B-15860.

3. The moisturizing cream or lotion according to claim 1 in which the bioemulsifier is selected from the group consisting of alpha-emulsan, apo-alpha-emulsan, psi-emulsan, apo-psi-emulsan, beta-emulsan, and lipoheteropolysaccharides.

4. In a moisturizing cream or lotion for topical application to the skin or scalp, the improvement which comprises incorporation in such moisturizing cream or lotion from at least about 0.1% to about 0.2% by weight of a bioemulsifier produced by an *Acinetobacter calcoaceticus* species, which bioemulsifier is characterized by (a) a specific Emulsification Activity of at least about 90 units per milligram; (b) the ability to remove sebum; and (c) the ability to interfere with microbial adhesion on skin or hair.

5. The moisturizing cream or lotion according to claim 4 in which the *Acinetobacter calcoaceticus* is selected from the group consisting of *Acinetobacter calcoaceticus* ATCC 31012, *Acinetobacter calcoaceticus* NRRL B-15616, *Acinetobacter calcoaceticus* NRRL B-15847, *Acinetobacter calcoaceticus* NRRL B-15848, *Acinetobacter calcoaceticus* NRRL B-15849, *Acinetobacter calcoaceticus* NRRL B-15850, and *Acinetobacter calcoaceticus* NRRL B-15860.

6. The composition according to claim 4 in which the bioemulsifier is selected from the group consisting of alpha-emulsan, apo-alpha-emulsan, psi-emulsan, apo-psi-emulsan, beta-emulsan, and lipoheteropolysaccharides.

7. In a moisturizing cream or lotion for topical application to skin or scalp, the improvement which comprises incorporating in such moisturizing cream or lotion from about 0.05% by weight to about 0.20% by weight of a viscoemulsan produced by an *Acinetobacter calcoaceticus* species, which viscoemulsan (a) is immunologically cross-reactive with antibodies against a bioemulsifier produced by an *Acinetobacter calcoaceticus* species; and (b) does not exhibit bioemulsifier activity.

8. A moisturizing cream or lotion according to claim 7 in which the viscoemulsan is produced by *Acinetobacter calcoaceticus* ATCC 31926.

9. A method of improving or ameliorating dry skin conditions which comprises applying to the affected skin a moisturizing cream or lotion into which at least about 0.02% by weight of a bioemulsifier produced by an *Acinetobacter calcoaceticus* species has been incorporated, which bioemulsifier is characterized by (a) a specific emulsification activity of at least about 25 units per milligram; (b) the ability to remove sebum; and (c) the ability to interfere with microbial adhesion on skin or hair.

10. The method according to claim 9 in which the bioemulsifier is alpha-emulsan.

11. In a mud mask formulation, the improvement which comprises the addition to such mud mask formulation of about 0.05% by weight to about 0.2% by weight of a bioemulsifier produced by an *Acinetobacter calcoaceticus* species, which bioemulsifier is characterized by (a) a specific emulsification activity of at least about 25 units per milligram; (b) the ability to remove sebum; and (c) the ability to interfere with microbial adhesion on skin or hair.

12. The mud mask according to claim 11 in which the bioemulsifier is alpha-emulsan.

* * * * *